United States Patent [19]

Leon-Pekarek

[11] 4,336,246
[45] Jun. 22, 1982

[54] HAIR MAKEUP PRODUCTS

[75] Inventor: Diane Leon-Pekarek, Sloatsburg, N.Y.

[73] Assignee: Avon Products, Inc., Suffern, N.Y.

[21] Appl. No.: 136,776

[22] Filed: Apr. 3, 1980

[51] Int. Cl.³ .................. A61K 7/06; A61K 31/74; A61K 7/13
[52] U.S. Cl. .................. 424/70; 424/63; 424/64; 424/78; 424/DIG. 2; 424/DIG. 5; 8/495; 8/405
[58] Field of Search ............ 424/63, 64, 61, 70, 424/34, 362, DIG. 2, DIG. 1; 8/495, 405

[56] References Cited

U.S. PATENT DOCUMENTS 2,936,245  5/1960  Osipow et al. .................. 106/189
3,485,915  12/1969  Gerstein et al. .................. 424/31

FOREIGN PATENT DOCUMENTS 2817325  1/1979  Fed. Rep. of Germany.

*Primary Examiner*—Donald B. Moyer
*Attorney, Agent, or Firm*—Sigalos & Levine

[57] ABSTRACT

A cosmetic product such as a hair makeup product comprising a waxy base, one or more color additives, a volatile solvent, and a film-forming resin composition comprising pentaerythritol rosinate in combination with either ethyl hydroxyethyl cellulose or a polyvinyl alkyl ether or mixtures thereof.

4 Claims, No Drawings

HAIR MAKEUP PRODUCTS

BACKGROUND OF THE INVENTION

Cosmetic products, specifically hair makeup products are presently available that impart a temporary sheen and/or color to the hair and which can be removed by shampooing. These are ordinarily in the form of crayons, creams, aerosols or liquids, but whatever the form, are unsatisfactory in that they give the treated hair a dull finish and/or are transferable. More importantly, the present hair products are not sufficiently waterproof. Thus, when exposed to rain, for example, the conventional hair products tend to run and smear.

It has been suggested to render makeup formulations waterproof, oilproof to an extent and long wearing by utilizing one or more resins such as ethyl hydroxyethyl cellulose or acrylic copolymers alone or in combination with an aromatic hydrocarbon resin. When ethyl hydroxyethyl cellulose is used in such prior formulations, it must be present in an amount of about at least 1.00% of the composition by weight in order to achieve the above desired characteristics. One feature of the present invention is the surprising discovery that significantly lower levels of ethyl hydroxyethyl cellulose may be combined with other film forming resins, which when combined with a waxy base, one or more color additives and volatile solvents, yields a commercially satisfactory hair makeup product which is waterproof, and highly resistant to removal by abrasion, and has some oil resistance. Products with acrylic copolymers, while water resistant, are not waterproof and, additionally, leave a dull finish when applied to the hair.

SUMMARY OF THE INVENTION

The present invention overcomes the problems of existing products to provide novel hair makeup products which, after application, dry to lustrous, waterproof, smearproof finishes which will not transfer and yet are easily removed by shampooing the hair.

Briefly, the present invention comprises hair makeup products comprising a waxy base, one or more color additives, volatile solvents, and a film-forming resin composition comprising pentaerythritol rosinate in combination with ethyl hydroxyethyl cellulose or a polyvinyl alkyl ether or mixtures thereof.

DETAILED DESCRIPTION

The instant invention is applicable to a wide variety of cosmetic products, but will be specifically discussed in connection with hair makeup products. Also, while the instant invention is applicable to any hair makeup product form, such as aerosol, crayon, pencil, cream, or liquid which can incorporate volatile solvents, it will be described in connection with creams and crayons (sticks) which are the preferred forms.

The essential components of the products of this invention are a waxy base, one or more color additives, volatile solvents, and a film-forming resin composition. Of these, the waxy base, the one or more color additives, and volatile solvents can be any conventionally used in hair makeup products.

As to the waxy base constituent, it can consist of suitable waxes, oils, semi-solid lipids, or mixtures thereof. Examples are carnauba wax, microcrystalline wax, ozokerite wax, candelilla wax, beeswax, isopropyl myristate, paraffin, castor oil, mineral oil, vegetable oils, lanolin or lanolin derivatives such as isopropyl lanolate, or mixtures thereof. The amount used in the product varies widely, with minor amounts in liquid products and larger amounts, about 20% by weight of the product, in stick (solid rod) products.

With respect to the color additives, these can be any desired or commonly-used cosmetically suitable dye, pigment, metallic powder, pearlescent material, or mixtures thereof to give the desired color, sheen or makeup effect. For coloring gray hair, for example, pigments giving the hair a blonde, black, red, or brunette color can be used. For highlighting the hair, metallic powders such as bronze and aluminum powders can be used to give gold and silver frosting. The amount used can vary widely and is dependent primarily upon the color effect it is desired to obtain.

The one or more cosmetically acceptable volatile solvents are preferably mineral spirits, isoparaffins, or petroleum distillates. Volatile silicones (such as cyclomethicone) or alcohols can be employed alone or in combination with each other or with any of the preferred solvents or mixtures of preferred solvents. The solvent comprises from about 30% by weight to 50% by weight and higher of the product dependent upon the physical form of the product, i.e., cream, stick, liquid or the like.

In accordance with the present invention, the critical component is the film-forming resin composition which comprises pentaerythritol rosinate in combination with either ethyl hydroxyethyl cellulose or a polyvinyl alkyl ether, or mixtures thereof. It is preferred to utilize all three resins. The polyvinyl alkyl ether is preferably polyvinyl isobutyl ether, although other ethers such as polyvinyl methyl ether or polyvinyl ethyl ether may be used as well alone or in combination with each other or with polyvinyl isobutyl ether.

In addition to these components, other additives conventionally used in the makeup formulation art can also be included in the products of this invention for their usual effect and in their usual amounts. Examples are gellants such as Quaternium 18 Hectorite, antioxidants such as butylated hydroxyanisole, plasticizers such as dibutyl phthalate, stabilizers such as polyoxyethylene stearate (PEG (40) stearate), and fragrances.

While the proportions of essential components will vary, dependent upon the form of the product, in all instances, whether cream or stick, the film-forming compositions are used in a range of from about 1% to about 30% by weight, based on the total weight of the product. The individual resins are adjusted within the ranges set forth below to give the desired properties.

|  | % By Weight |
| --- | --- |
| Pentaerythritol rosinate | 1–20 |
| Ethyl Hydroxyethyl cellulose | 0.01–0.9 |
| Polyvinyl alkyl ether | 0.01–8 |

Generally, the higher levels of the resins are used in the stick products and the lower levels in the cream products.

It will be understood that the products of this invention can be used to temporarily color hair shafts, streak or highlight hair, cover new hair growth, or gray, or otherwise give a new color, lustrous finish, or any other makeup or cosmetic effect to hair in any manner desired by the user. When the user desires to remove the color or finish applied, only shampooing of the hair is required to effect such removal.

The invention will be further illustrated in connection with the following examples which are set forth for purposes of illustration only and in which proportions are in percentages by weight.

EXAMPLE 1

A cream hair makeup product was prepared by admixing the following components:

| | % By Weight |
| --- | --- |
| Petroleum Distillates | 51.29 |
| Quaternium 18 Hectorite | 4.19 |
| Pentaerythritol Rosinate | 2.60 |
| Polyvinyl Isobutyl Ether | 0.29 |
| Ethyl Hydroxyethyl Cellulose | 0.47 |
| Ozokerite | 2.30 |
| Carnauba Wax | 3.75 |
| Lanolin-Anhydrous | 0.55 |
| Isopropyl Lanolate | 0.35 |
| Dibutyl Phthalate | 0.13 |
| BHA | 0.05 |
| PEG (40) Stearate | 0.07 |
| Metallic Powder | 32.00 |
| Propylene Carbonate | 1.26 |
| Fragrance | 0.70 |

The product is applied to hair and when dry gives a lustrous finish that is waterproof and highly resistant to removal by abrasion, i.e., it does not smear, smudge, or transfer. It is readily removed from the hair by shampooing.

EXAMPLE 2

A stick (solid rod) hair makeup product was prepared by admixing the same components as in Example 1, but in the proportions set forth below.

| | % By Weight |
| --- | --- |
| Petroleum Distillates | 32.38 |
| Quaternium 18 Hectorite | 1.58 |
| Pentaerythritol Rosinate | 3.72 |
| Polyvinyl Isobutyl Ether | 0.40 |
| Ethyl Hydroxyethyl Cellulose | 0.86 |
| Ozokerite | 6.29 |
| Carnauba Wax | 10.32 |
| Lanolin-Anhydrous | 1.45 |
| Isopropyl Lanolate | 0.97 |
| Dibutyl Phthalate | 0.23 |
| BHA | 0.05 |

-continued

| | % By Weight |
| --- | --- |
| PEG (40) Stearate | 0.19 |
| Metallic Powder | 41.08 |
| Propylene Carbonate | 0.48 |
| Fragrance | — |

This product also shows a lustrous finish and compared to the product of Example 1, equally good wear and waterproof properties when applied to hair.

In the commercial distribution of the instant hair makeup products, as in other cosmetic products containing large proportions of volatile solvents, they must be packaged in containers which prevent or minimize loss of the volatile materials.

While the invention has been described in connection with a preferred embodiment in the form of a hair makeup product, it will be appreciated by those skilled in this art that the principles of the present invention are applicable to other cosmetic products as well, such as foundation, blush, eye shadow, mascara, eye liner, brow makeup, leg makeup, lip makeup, and the like. Accordingly, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A hair makeup product comprising a waxy base, at least one color additive, at least one volatile solvent, and from about 1 to 30% by weight, based on the total weight of the product, of a film-forming resin composition comprising pentaerythritol rosinate and a resin selected from ethyl hydroxyethyl cellulose, a polyvinyl alkyl ether, or mixtures thereof.

2. The product of claim 1 wherein the film-forming resin composition consists essentially of pentaerythritol rosinate, ethyl hydroxyethyl cellulose, and polyvinyl alkyl ether.

3. The product of claim 2 wherein the waxy base is a mixture of ozokerite, carnauba wax, anhydrous lanolin, and isopropyl lanolate, the solvent is petroleum distillates, and the polyvinyl alkyl ether is polyvinyl isobutyl ether.

4. The product of claim 3 wherein the film-forming composition consists of from about 1 to 20% by weight pentaerythritol rosinate, about 0.01 to 0.9% by weight ethyl hydroxyethyl cellulose, and about 0.01 to 8% by weight polyvinyl isobutyl ether, based on the total weight of the product.

* * * * *